(12) United States Patent
Akazawa et al.

(10) Patent No.: US 9,089,581 B2
(45) Date of Patent: Jul. 28, 2015

(54) METHOD FOR PRODUCING DRY EARTHWORM POWDER

(71) Applicants: WAKI PHARMACEUTICAL CO., LTD., Nara-ken (JP); NATIONAL INSTITUTE OF TECHNOLOGY, Hachioji, Tokyo (JP)

(72) Inventors: Shin-ichi Akazawa, Nagaoka (JP); Shinnosuke Wakimoto, Yamatotakada (JP); Toshinori Watanabe, Nara-ken (JP)

(73) Assignees: WAKI PHARMACEUTICAL CO., LTD., Nara-ken (JP); NATIONAL INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 14/466,018

(22) Filed: Aug. 22, 2014

(65) Prior Publication Data

US 2015/0064269 A1 Mar. 5, 2015

(30) Foreign Application Priority Data

Sep. 3, 2013 (JP) .................................. 2013-182399

(51) Int. Cl.
*A61K 35/62* (2006.01)
*A61K 9/14* (2006.01)

(52) U.S. Cl.
CPC .. *A61K 35/62* (2013.01); *A61K 9/14* (2013.01)

(58) Field of Classification Search
USPC ......................................................... 424/520
IPC ..................................................... A61K 35/62
See application file for complete search history.

(56) References Cited

U.S. PATENT DOCUMENTS

| | | | |
|---|---|---|---|
| 4,568,545 A * | 2/1986 | Mihara et al. | 424/94.64 |
| 5,186,944 A * | 2/1993 | Ishii et al. | 424/520 |
| 5,576,026 A * | 11/1996 | Charter et al. | 424/520 |
| 8,394,417 B2 | 3/2013 | Ishii et al. | |
| 2008/0206352 A1 * | 8/2008 | Li | 424/520 |
| 2009/0238891 A1 * | 9/2009 | Ishii et al. | 424/520 |
| 2011/0086106 A1 * | 4/2011 | Ishii et al. | 424/520 |
| 2012/0294950 A1 | 11/2012 | Ishii | |

FOREIGN PATENT DOCUMENTS

| | | | |
|---|---|---|---|
| CN | 1349766 | * | 5/2002 |
| CN | 1 587 398 A | | 3/2005 |
| CN | 102100825 | * | 6/2011 |
| CN | 102389563 | * | 3/2012 |
| CN | 102397394 | * | 4/2012 |
| CN | 102988577 | * | 3/2013 |
| CN | 102988611 | * | 3/2013 |
| CN | 103239706 A | | 8/2013 |
| JP | 2001-158746 A | | 6/2001 |
| JP | 4808822 B1 | | 11/2011 |
| JP | 4886017 B2 | | 2/2012 |
| JP | 2012-219070 A | | 11/2012 |

OTHER PUBLICATIONS

Japanese Office Action for JP 2013-182399 dated Jan. 28, 2104.
Chinese Office Action issued Mar. 12, 2015 in Chinese Patent Application No. 201410440464.4.

* cited by examiner

*Primary Examiner* — Chris R Tate
(74) *Attorney, Agent, or Firm* — Sughrue Mion, PLLC

(57) ABSTRACT

[Task] A method for producing dry earthworm powder, in which there is no risk of reduction of the enzymatic activity of earthworms and the enzymatic activity of the dry earthworm powder obtained therefrom is increased, is provided.

[Means for Resolution] Disclosed is a method for producing dry earthworm powder, in which earthworms which have been subjected to a treatment for removing casting soil are used as a raw material to produce dry earthworm powder, the living organisms of the earthworms or crushed products thereof which have been subjected to a treatment for removing casting soil are subjected to a pressurization treatment under a pressure condition of 10 MPa to 500 MPa and a temperature condition of 0° C. to 70° C., and the earthworms or crushed products thereof after the pressurization treatment are used as a raw material of the dry earthworm powder.

9 Claims, 2 Drawing Sheets

Fig. 1

|  |  | Earthworms in the related art | Earthworms according to the present process |
|---|---|---|---|
| Sample 1 | General bacteria | Not measurable | 890000000 |
|  | Escherichia coli | Not measurable | 300 |
| Sample 2 | General bacteria | Not measurable | 810000000 |
|  | Escherichia coli | Not measurable | 300 |
| Sample 3 | General bacteria | Not measurable | 720000000 |
|  | Escherichia coli | Not measurable | 200 |
| Sample 4 | General bacteria | Not measurable | 680000000 |
|  | Escherichia coli | Not measurable | 100 |
| Sample 5 | General bacteria | Not measurable | 780000000 |
|  | Escherichia coli | Not measurable | 200 |

Fig. 2

| Sample | Protein concentration (mg/mL) | Total protein (mg) | Total activity (units) | | Specific activity (units/mg) | |
|---|---|---|---|---|---|---|
|  |  |  | S-2251 | S-2288 | S-2251 | S-2288 |
| Not treated | 14 | 260 | 8.7±1.0 | 14±1 | 0.033±0.004 | 0.053±0.006 |
| Vaporized ethanol | 14 | 210 | 15±1 | 27±4 | 0.073±0.006 | 0.13±0.02 |

Fig. 3

| Sample | Protein concentration (mg/mL) | Total protein (mg) | Total activity (units) | | Specific activity (units/mg) | |
|---|---|---|---|---|---|---|
| | | | S-2251 | S-2288 | S-2251 | S-2288 |
| Not treated | 19 | 540 | 7.7±0.8 | 15±2 | 0.014±0.001 | 0.027±0.004 |
| 10% NaCl | 15 | 370 | 22±2 | 33±2 | 0.059±0.005 | 0.090±0.006 |
| 0.05% NaClO | 18 | 550 | 20±2 | 41±8 | 0.037±0.005 | 0.075±0.015 |
| 0.1% NaClO | 20 | 560 | 27±6 | 48±12 | 0.049±0.011 | 0.086±0.021 |
| 0.25% NaClO | 14 | 440 | 40±5 | 66±3 | 0.091±0.012 | 0.15±0.006 |
| 0.5% NaClO | 16 | 530 | 45±4 | 80±4 | 0.086±0.007 | 0.15±0.007 |

Fig. 4

| Sample | Number of general bacteria | Number of Escherichia coli |
|---|---|---|
| Not pressurization-treated | 128000 | 71000 |
| 50°C, 100 MPa, 1 hour | 30 | Negative |
| 50°C, 100 MPa, 2 hours | Negative | Negative |

Fig. 5

| Sample | Protein concentration (mg/mL) | Total activity (units) | | Specific activity (units/mg) | |
|---|---|---|---|---|---|
| | | S-2251 | S-2288 | S-2251 | S-2288 |
| Not pressurization-treated | 17 | 42±4.1 | 92±4.2 | 0.10±0.01 | 0.22±0.01 |
| 50°C, 100MPa, 1h | 4.3 | 44±5.3 | 100±4.3 | 0.44±0.05 | 1.0±0.04 |
| 50°C, 100MPa, 2h | 4.2 | 54±6.2 | 132±10 | 0.48±0.06 | 1.2±0.09 |

METHOD FOR PRODUCING DRY EARTHWORM POWDER

TECHNICAL FIELD

The present invention relates to a method for producing dry earthworm powder, in which earthworms which have been subjected to a treatment for removing casting soil are used as a raw material to produce dry earthworm powder.

BACKGROUND ART

Culture of earthworms which will be a raw material for dry earthworm powder used for health food or drugs is carried out by supplying cow manure, food waste, or the like as a feed in addition to soil in a culture bed including the soil. Generally, *Escherichia coli* or general bacteria are bred in the soil, and many harmful substances such as arsenic or heavy metals are contained in the soil as well as the feed supplied to earthworms. Thus, the earthworms accumulate bacteria or a harmful substance in their bodies by eating soil or feed during the growth. Therefore, it is required to remove bacteria or a harmful substance from earthworms so as to avoid adverse effects on human bodies in the production of dry earthworm powder.

In the related art, as a method for producing dry earthworm powder, from which bacteria or a harmful substance has been removed, a method in which body cavity fluids (coelomic fluid) containing casting soil and a harmful substance in the bodies of the earthworms are removed, bacteria or a harmful substance is thus removed from the earthworms, and these earthworms are used as a raw material for dry earthworm powder has been known. For example, a method in which casting soil or body cavity fluids are removed from the bodies of earthworms by a step of leaving the living organisms of the earthworms to stand in a bright place for a long period of time and a step of sprinkling powder of acids such as citric acid onto the earthworms or dipping the earthworms in aqueous solutions of the acids; the earthworms are then crushed; and the crushed products thereof are freeze-dried to produce dry earthworm powder, from which bacteria or a harmful substance has been removed, has been known (see Patent Document 1).

In addition, a method in which bacteria are further removed by subjecting the dry earthworm powder produced to heat sterilization has also been known (see Patent Document 2).

RELATED ART DOCUMENT

Patent Document

[Patent Document 1] Japanese Patent No. 4808822
[Patent Document 2] Japanese Patent No. 4886017

DISCLOSURE OF THE INVENTION

Problem that the Invention is to Solve

The pharmacological action of dry earthworm powder as health food or drugs is due to the function of an enzyme in an earthworm, and since a higher enzymatic activity of dry earthworm powder leads to a higher pharmacological action, it is demanded that the enzymatic activity of the dry earthworm powder produced be high.

However, when heat sterilization is carried out as in the related art, enzymes are generally susceptible to heat, and as a result, the enzymatic activities are inevitably reduced.

Taking this circumstance into consideration, a main object of the present invention is to provide a method for producing dry earthworm powder, in which there is no risk of reduction of the enzymatic activities of earthworms and the enzymatic activity of the dry earthworm powder obtained therefrom is increased, by employing a rational sterilization method.

Means for Solving the Problem

A first characteristic configuration of the present invention relates to a method for producing dry earthworm powder. This is a method for producing dry earthworm powder, in which earthworms which have been subjected to a treatment for removing casting soil are used as a raw material to produce dry earthworm powder, in which the living organisms of the earthworms or crushed products thereof which have been subjected to a treatment for removing casting soil are subjected to a pressurization treatment under a pressure condition of 10 MPa to 500 MPa and a temperature condition of 0° C. to 70° C., and the earthworms or crushed products thereof after the pressurization treatment are used as a raw material for the dry earthworm powder.

That is, according to the present configuration, the earthworms or crushed products thereof which have been subjected to a treatment for removing casting soil can be reliably sterilized by a pressurization treatment. Therefore, as compared with a heat sterilization having a risk of reduction of the enzymatic activities, there is no risk of reduction of the enzymatic activities, and further, the enzymatic activities of the earthworms or crushed products thereof can be increased through the pressurization treatment.

Moreover, the self-digestion of the earthworms is promoted by an increase in the enzymatic activities of the earthworms through the pressurization treatment, thereby allowing the skin of the earthworms to be lysated by the self-digestion during the pressurization treatment, a step of removing the skin of the earthworms by filtration or the like, in which a step that had been required before a processing into dry earthworm powder in the related art, can be omitted. Thus, problems such as loss of active ingredients due to the step of removing the skin such as filtration and reduction of the yield of a supernatant from which dry earthworm powder is collected can be avoided.

In addition, odor of earthworms, which is generated from a step of crushing the earthworms, or the like to a processing into dry powder, can be effectively reduced by a pressurization treatment, and thus, the working environment can also be improved. Further, by carrying out the pressurization treatment under the temperature condition as described above, the sterilization of earthworms can be carried out more effectively under a temperature condition for preventing the reduction of the enzymatic activity by heating. In addition, the pressure condition for the pressurization treatment is more preferably from 100 MPa to 200 MPa.

The second characteristic configuration of the present invention is a configuration suitable for the practice of the first characteristic configuration, in which casting soil is removed from the bodies of earthworms by subjecting the earthworms to irradiation of heat rays by a heater as a treatment for removing casting soil, and the living organisms of the earthworms or crushed products thereof after the removal of the casting soil are subjected to the pressurization treatment.

That is, the earthworms have a characteristic of excreting casting soil or the like from their bodies in order to protect the bodies of the earthworms from dehydration when their skins are dry. Thus, according to these configurations, the skin of the earthworms is dried with the irradiation of heat rays by a heater to promote the discharge of the casting soil from the earthworms, and further, as the body temperatures of the earthworms rise through the irradiation by the heater, the motion is activated and the efficiency in the discharge of casting soil can be increased. Accordingly, it is possible to carry out the removal of casting soil from the bodies of the earthworms efficiently in a very short period of time.

That is, since it is possible to carry out the removal of casting soil in a short period of time according to the present configuration, the damages applied to the earthworms in the removal of casting soil can be reduced, and thus, the reduction of the enzymatic activity due to the damages to the earthworms can be effectively inhibited.

The third characteristic configuration of the present invention is a configuration suitable for the practice of the second characteristic configuration, in which irradiation of heat rays onto earthworms by the heater, and removal of the casting soil excreted by the earthworms due to the irradiation of heat rays or removal of the bed materials on the surface layer of a growth bed for growing earthworms are carried out alternatively.

That is, with the irradiation of heat rays by a heater, the earthworms put on casting soil excreted by themselves or crawl into the bed materials of a growth bed for growing the earthworms, and the irradiation of heat rays by a heater is thus interfered with by the casting soil or bed materials on the surface layer. On the contrary, according to the configuration as described above, since the irradiation of heat rays by a heater, the removal of the casting soil put on by the earthworms, or the removal of the bed materials on the surface layer in the upper part of the crawling earthworms are carried out alternatively, the earthworms can be subjected to removal of the casting soil from the bodies of the earthworms more effectively while the casting soil or bed materials on the surface layer do not interfere with the irradiation of heat rays by a heater.

That is, according to the present configuration, the removal of the casting soil can be more effectively carried out as described above, and therefore, the damage applied to the earthworms in the removal of the casting soil can be reduced, and thus, the reduction of the enzymatic activity due to the damage to the earthworms can be more effectively inhibited.

The fourth characteristic configuration of the present invention is a configuration suitable for the practice of the first to third characteristic configurations, in which the casting soil and the body cavity fluids are removed from the bodies of the earthworms by exposing the earthworms to a vaporized (evaporized) volatile organic solvent as a treatment for removing casting soil, and the living organisms of the earthworms or crushed products thereof after the removal of the casting soil and the body cavity fluids are subjected to the pressurization treatment.

That is, according to the configuration, by using the earthworms, which have been subjected to a treatment for removing casting soil/body cavity fluids using a volatile organic solvent, as a raw material for dry earthworm powder, dry earthworm powder having a high enzymatic activity (that is, a high pharmacological action) can be obtained, as compared with a case of using earthworms which have not been subjected to the same treatment as a raw material.

Moreover, according to the configuration, the casting soil and the body cavity fluids can also be safely removed from the bodies of the earthworms by applying a stimulus to the earthworms by a volatile organic solvent having less harmful to earthworms than acids such as citric acid.

Furthermore, according to this configuration, the earthworms are exposed to a volatile organic solvent which has been vaporized, and therefore, as compared with a case where the earthworms are dipped in a liquid volatile organic solvent, there is no case where the body temperatures of the earthworms are significantly lowered, and thus, the casting soil and the body cavity fluids can be efficiently removed from the bodies of the earthworms while not causing a reduction of the efficiency in the discharge of casting soil/body cavity fluids of the earthworms due to the lowered body temperatures of the earthworms.

In addition, if a solvent having a sterilization action is chosen from volatile organic solvents, it is possible to carry out a treatment for removing casting soil/body cavity fluids according to the present configuration and the sterilization of earthworms at the same time.

The fifth characteristic configuration of the present invention is a configuration suitable for the practice of the first to third characteristic configurations, in which the casting soil and the body cavity fluids are removed from the bodies of the earthworms by dipping the earthworms in an alkaline solution as a treatment for removing casting soil, and the living organisms of the earthworms or crushed products thereof after the removal of the casting soil and the body cavity fluids are subjected to the pressurization treatment.

That is, according to the configuration, by using the earthworms, which have been subjected to a treatment for removing casting soil/body cavity fluids using an alkaline solution, as a raw material for dry earthworm powder, dry earthworm powder having a high enzymatic activity (that is, a high pharmacological action) can be obtained, as compared with a case of using earthworms which have not been subjected to the same treatment as a raw material.

Moreover, according to the configuration, by applying a stimulus to the earthworms by an alkaline solution being less harmful to earthworms than acids such as citric acid, the casting soil and the body cavity fluids can also be safely removed from the bodies of the earthworms.

In addition, if a solution having a sterilization action is chosen from alkaline solutions, it is possible to carry out a treatment for removing casting soil/body cavity fluids according to the present configuration and the sterilization of earthworms at the same time.

BRIEF DESCRIPTION OF THE DRAWINGS

FIG. 1 is a table showing the number of general bacteria and the number of *Escherichia coli* of earthworms grown in a growth exclusive bed.

FIG. 2 is a table showing a change in the enzymatic activities of earthworms which have been subjected to a treatment for removing casting soil/body cavity fluids with exposure to a vaporized volatile organic solvent.

FIG. 3 is a table showing a change in the enzymatic activities of earthworms which have been subjected to a treatment for removing casting soil/body cavity fluids by the dipping in an alkaline solution.

FIG. 4 is a table showing a change in the number of general bacteria and the number of *Escherichia coli* of earthworms by a pressurization treatment.

FIG. 5 is a table showing a change in the enzymatic activities of earthworms by a pressurization treatment.

DESCRIPTION OF EMBODIMENTS

The method for producing dry earthworm powder of the present invention can be divided into a step of culturing earthworms, a step of a treatment for removing casting soil of the earthworms, and a step of producing dry earthworm powder, and each of the steps will be described hereinbelow. Further, in the present Examples, *Eisenia fetida* pertaining to the family Lumbricidae was used as the earthworm.

<Step of Culturing Earthworms>

In the present invention, earthworms are separated into earthworms for breeding that lay eggs and earthworms for growth that are used as a raw material for dry earthworm powder, and grown. Further, the earthworms for breeding are bred in a breeding exclusive bed and allowed to lay eggs, and the earthworms for growth are bred in a growth exclusive bed to carry out culture of the earthworms.

The breeding exclusive bed is prepared by spreading bed materials in a container. However, the bed materials are not particularly limited and the breeding exclusive bed may be formed of soil as for the culture of earthworms in the related art.

Furthermore, the growth exclusive bed is prepared by spreading plant fiber materials as a bed material in a container. Further, a variety of plant fiber materials such as palm, pineapple, coconut, water moss, peanut shells, and waste pulp can be employed.

In the production of a growth exclusive bed, in which the plant fiber materials are used as the bed materials, first, the plant fiber materials are crushed, mineral fractions such as vitamin and calcium are then incorporated therein, and the crushed products are dipped in a treatment liquid adjusted to around neutral pH values appropriate for an environment for growth of the earthworms, thereby incorporation of the mineral fractions and adjustment of the pH of the crushed products is carried out. In addition, the crushed products are dried to adjust the water content, and a growth exclusive bed is prepared with the dried products finally obtained.

The plant fiber materials used as the raw materials for the growth exclusive bed have a smaller number of bacteria than in soil. Further, by a step of dipping the crushed products of the plant fiber materials in the treatment liquid, arsenic or heavy metals in the crushed products are eluted in the treatment liquid, and thus, harmful substances such as arsenic and heavy metals are separated off from the plant fiber materials which are the crushed products. In addition, since the plant fiber materials having a small number of bacteria, from which the harmful substance has been removed, are used as the raw materials, the growth exclusive bed has a small number of bacteria and harmful substance. Accordingly, by this growth exclusive bed, the earthworms for growth can be bred in a clear environment.

In the step of culturing the earthworms in the present invention, earthworms for breeding are fed with a separate feed in a breeding exclusive bed and bred to lay eggs, and the eggs laid by the earthworms for breeding are transferred to the growth exclusive bed to be hatched in the growth exclusive bed or the earthworms hatched in the breeding exclusive bed are transferred to the growth exclusive bed. In addition, the earthworms in the growth exclusive bed are taken as the earthworms for growth and bred without supplying a separate feed.

Since nutrients such as calcium, protein, and organic decomposition products are required for laying eggs, the breeding of earthworms for breeding in a breeding exclusive bed is carried out while giving a feed to lay eggs efficiently by providing the nutrients. Further, a variety of feeds such as strained lees of Shochu, ground coffee beans, and waste mushroom beds of mushrooms can be employed.

Furthermore, in the breeding of the earthworms for growth in the growth exclusive bed, the growth exclusive bed has plant fiber materials having a smaller number of bacteria, from which a harmful substance has been separated, as the raw materials, and as a result, accumulation of bacteria or a harmful substance in the bodies of the earthworms for growth can be effectively inhibited.

That is, in the case where earthworms are grown in soil in which bacteria are generally bred and many harmful substances such as arsenic and heavy metals are contained, the earthworms eat the soil during the growth and accumulate the bacteria or a harmful substance in their bodies. On the contrary, in the case where earthworms for growth are grown in a growth exclusive bed, since the earthworms for growth eat the plant fiber materials that are bed materials of the growth exclusive bed as a feed and the plant fiber materials have a smaller number of bacteria, from which a harmful substance has been separated, accumulation of bacteria or a harmful substance in the bodies of the earthworms for growth can be effectively inhibited.

Moreover, since the earthworms for growth are not desired to lay eggs, it is not necessary to provide nutrients required for laying eggs, and since the earthworms for growth are sufficiently grown by eating plant fiber materials, it is not necessary to provide a feed unlike that for the earthworms for breeding, in the growth of the earthworms for growth in the growth exclusive bed. By this, accumulation of harmful substances such as arsenic and heavy metals much contained in the feed in the earthworms through the feed and promotion of the breeding of bacteria of the plant fiber materials by the feed are avoided, and thus, accumulation of bacteria or harmful substance in the bodies of the earthworms for growth can be more effectively inhibited.

Furthermore, since mineral fractions are contained as the nutrients in the plant fiber materials eaten by the earthworms for growth by the step of dipping the treatment liquid, a problem that the earthworms for growth are not grown due to poor nutrition can be avoided.

FIG. 1 shows the number of general bacteria and the number of *Escherichia coli* of earthworms bred in a growth exclusive bed at 20° C. to 25° C. for 3 months by the present step. The growth exclusive bed in the present Example had palm fibers as a raw material. Specifically, in the growth exclusive bed, the palm fibers were crushed by a commercially available crusher, contaminants adhered are removed by sufficiently washing with tap water through a sterilizing filtration filter, and next, crushed products of palm fibers were dipped in a treatment liquid adjusted to around neutral pH values by incorporating mineral fractions such as vitamin and calcium for about 20 hours and the pH of the crushed products was adjusted while the mineral fractions are incorporated. Thereafter, crushed products thereof, which had been low-temperature dried at 20° C. to 40° C. for a long period of time, were spread in the container for the preparation. Further, in FIG. 1, the number of general bacteria and the number of *Escherichia coli* of the earthworms in the related art, which have been bred by providing a separate feed in a culture bed including soil, are compared. For five earthworms in each case of the earthworms in the present step and the earthworms in the related art, each earthworm was crushed by a homogenizer, and the number of bacteria was examined without the addition of a sterilization step.

Examination of the number of bacteria was carried out by plating a stock solution of an earthworm crushing solution and 1 mL of an earthworm crushing solution with had been diluted with sterile water onto a 3M Petrifilms AC Plate (manufactured by Sumitomo 3M Ltd.; 3M and Petrifilms are registered marks), culturing the plate in an incubator set at 30° C. for 48 hours, and then measuring the number of the colonies, in the case of examination of the number of general bacteria. Examination of the number of *Escherichia coli* was carried out by plating a stock solution of an earthworm crushing solution and 1 mL of an earthworm crushing solution with had been diluted with sterile water onto a 3M Petrifilms RCC Plate (manufactured by Sumitomo 3M Ltd.), culturing the plate in an incubator set at 35° C. for 24 hours, and then measuring the number of the colonies.

As shown in FIG. 1, for the earthworms in the related art, general bacteria and *Escherichia coli* have both been not measurable. The reason therefor is that the amount of bacteria of one billion or more is not measurable, which indicates that many bacteria are accumulated in the earthworms in the related art. To the contrary, the earthworms by the present step, which had been bred in the growth exclusive bed, are within a measurable range for both of general bacteria and *Escherichia coli*, which indicate that by the present step, accumulation of bacteria in the bodies could be effectively inhibited, as compared with the earthworms in the related art. In particular, taking into consideration that the number of earthworms in the related art is at least one billion or more in the case of *Escherichia coli*, it can be seen that the number is reduced by six digits or more. Thus, for the earthworms by the present step, which had been bred in the growth exclusive bed, accumulation of bacteria in the bodies can be effectively inhibited, as compared with the earthworms in the related art.

<Step of Casting Soil Removal Treatment for Earthworms>

This step of a treatment for removing casting soil for earthworms can be divided into (1) a step of removing casting soil with the irradiation by a heater, and subsequently (2-1) a step of removing the residual casting soil/body cavity fluids by the exposure to a vaporized volatile organic solvent, or (2-2) a step of removing the residual casting soil/body cavity fluids by dipping in an alkaline solution.

(1) Step of Removing Casting Soil with Irradiation by Heater

In the present step, using a characteristic of the earthworms to excrete casting soil or the like and put casting soil on in order to protect the bodies of the earthworms from dehydration when their skins are dry, the skin of the earthworms is dried with the irradiation of heat rays by a heater to promote the discharge of casting soil of the earthworms. In addition, as the body temperatures of the earthworms rise through the irradiation by the heater, the motion is activated and the efficiency in the discharge of casting soil can be further increased. Accordingly, it is possible to carry out the removal of casting soil from the bodies of earthworms for growth efficiently.

In a specific step, first, the growth exclusive bed, in which the earthworms for growth have been bred for a constant period, is transferred to a treatment chamber, and then the earthworms for growth exposed to a bright environment in the growth exclusive bed (in other words, the earthworms for growth exposed to the surface of the growth exclusive bed in a bright environment) are subjected to irradiation of heat rays by a heater such as an infrared ray heater from the upper part thereof.

In this case, the earthworms for growth dislike the irradiation of heat rays by a heater and crawl into the bed materials while excreting casting soil. Thus, by stopping the irradiation by the heater, the bed materials are stripped from the growth exclusive bed until the earthworms for growth are exposed to the surface of the growth exclusive bed (appear on the surface), and then the earthworms for growth exposed to the surface of the growth exclusive bed are again subjected to irradiation by the heater from the upper part thereof.

By carrying out the irradiation by the heater and the stripping of the bed materials alternatively and repeatedly, the earthworms for growth can be subjected to direct irradiation by a heater. Thus, the casting soil can be excreted efficiently, and at the same time, the earthworms for growth can be allowed to crawl into the lower part of the growth exclusive bed. Further, this operation is repeated until the state where the bed materials almost disappear from the growth exclusive bed and the earthworms for growth gather at the bottom of the growth exclusive bed.

Furthermore, even in the state where the earthworms for growth gather at the bottom of the growth exclusive bed, when the irradiation by the heater is carried out, there is no bed material into which the earthworms for growth can crawl, and accordingly, the earthworms for growth put on the casting soil excreted by themselves to block the irradiation by the heater. Thus, the irradiation by the heater is stopped, the casting soil is then stripped from the earthworms for growth, and the earthworms for growth are again subjected to irradiation by the heater from the upper part thereof.

By carrying out the irradiation by the heater and the stripping of the casting soil 2 to 3 times alternatively and repeatedly, the casting soil is effectively removed from the bodies of the earthworms for growth.

Thus, in the present step, by stripping the bed materials only in the parts into which the earthworms for growth crawl or stripping the casting soil put on by the earthworms for growth, and then subjecting the earthworms for growth to irradiation of heat rays by a heater, the removal of the casting soil from the bodies of the earthworms for growth can be efficiently carried out while the bed materials or casting soil do not interfere with the irradiation of heat rays by the heater.

Furthermore, in the present step, when not taking the trouble to take out the earthworms for growth from the growth exclusive bed to sort the earthworms for growth from the bed materials, it is possible to sort the earthworms for growth from the bed materials while carrying out the removal of the casting soil from the earthworms for growth with the irradiation by a heater. Therefore, this step is efficient as treatment because it does not involve such the trouble above.

Incidentally, the earthworms die when the body temperatures rise to a certain degree, and as a result, in the present step, in order to prevent the body temperature of the earthworms for growth from rising too high, the amount of heat irradiated by a heater should be set to a degree at which earthworms do not die and the heater should be used intermittently but be not used continuously for a long period of time.

(2-1) Step of Removing Residual Casting Soil/Body Cavity Fluids by Exposure to Vaporized Volatile Organic Solvent In the present step, stimuli are applied to the earthworms for growth by exposing the earthworms for growth obtained by washing the skin after the step of removing the casting soil with the irradiation by a heater to a vaporized volatile organic solvent, thereby the removal of the residual casting soil and the body cavity fluids from the earthworms for growth is carried out.

Since the body cavity fluids contain harmful substances such as arsenic and heavy metals in the body of earthworms, the harmful substances can be removed from the bodies of the earthworms for growth by removing the body cavity fluids.

Exposure to a vaporized volatile organic solvent is carried out by, for example, putting cotton wool containing a volatile organic solvent in a bottle, vaporizing the volatile organic solvent in the bottle, and spraying the vaporized volatile organic solvent to the earthworms for growth by means of a spraying means such as nozzles, equipped in the bottle.

By vaporizing the volatile organic solvent and subjecting the earthworms to exposure to the vaporized volatile organic solvent, there is no case where the body temperatures of the earthworms are significantly lowered, as compared with a case of dipping earthworms in a volatile organic solvent of a liquid, and therefore, the reduction of efficiency in the discharge of casting soil/body cavity fluids of the earthworms due to the lowered body temperatures of the earthworms is not caused in any case.

Incidentally, by using the earthworms which have been subjected to a treatment for removing casting soil/body cavity fluids using a volatile organic solvent as a raw material for dry earthworm powder, it is possible to obtain dry earthworm powder having a high enzymatic activity (that is, a high pharmacological action), as compared with a case of using earthworms which have not been subjected to the same treatment as a raw material.

The volatile organic solvent used in the present step is not particularly limited, and may be any one of an alcohol, methanol, hexane, triethylamine, methyl acetate, chloroform, and the like, but the alcohol is particularly preferred from the viewpoint of toxicity or safety.

Furthermore, when the alcohol is used as a volatile organic solvent, removal of the residual casting soil/body cavity fluids and sterilization of skin of earthworms can be carried out at the same time.

FIG. 2 shows a change in the enzymatic activities of earthworms for growth, which have been subjected to removal of casting soil/body cavity fluids by the present step. Specifically, the earthworms for growth, which had been bred in a growth exclusive bed, were first subjected to removal of casting soil with the irradiation by a heater in the similar manner to the step of (1), and in the step of removing the residual casting soil/body cavity fluids of (2-1), ethanol was used as a volatile organic solvent, and the earthworms for growth were exposed to ethanol that had been vaporized at 50° C. and subjected to removal of the residual casting soil/body cavity fluids. Then, the earthworms for growth were crushed by a homogenizer, crushed products thereof were suspended in pure water, and the activity of the supernatant extracted by a centrifuge from the suspension was measured. Further, the amount of protein was also measured in order to determine a specific activity. In addition, as a control for comparison, the activity of the supernatant extracted from earthworms which had not been subjected to a treatment for exposure to vaporized ethanol was also measured.

In the measurement of the enzymatic activity, the plasmin activity and the t-PA activity were measured, using a plasmin substrate (S-2251: manufactured by Sekisui Medical Co., Ltd.) and a tissue plasminogen activator (t-PA) substrate (S-2288: manufactured by Sekisui Medical Co., Ltd.) as a fibrinolytic activity substrate. The amount of 1 µmol of p-nitroaniline (pNA) released for one minute was taken as a 1 unit, and the absorption wavelength at 405 nm was measured at 37° C. using a CORONA GRATING MICROPLATE READER SH-9000 (manufactured by Corona Electric Co., Ltd.). The composition of the reaction solution was as follows: 0.25 mM substrate, 50 mM Tris-HCl, and an appropriate amount of an enzyme solution.

The amount of protein was measured by a Bradford method. Specifically, the amount was determined at a wavelength of 595 nm, using a CORONA GRATING MICROPLATE READER SH-9000 (manufactured by Corona Electric Co., Ltd.) and a Bio-Rad protein assay reagent available from Bio-Rad. To create a calibration curve, bovine serum albumin (BSA) was used.

As shown in FIG. 2, the earthworms which had been exposed to vaporized ethanol had an increase in a total activity of the plasmin activity and the t-PA activity by little less than 2 times, and an increase in the specific activity by 2 times or more, as compared with the earthworms which had not been subjected to a treatment for exposure to vaporized ethanol. Thus, by carrying out the step of removing the residual casting soil/body cavity fluids by exposure to a vaporized volatile organic solvent in the present invention, it is possible to carry out the removal of the residual casting soil/body cavity fluids as well as the increase in the enzymatic activity of the earthworms for growth.

(2-2) Step of Removing Residual Casting Soil/Body Cavity Fluids by Dipping in Alkaline Solution In the present step, stimuli are applied to the earthworms for growth by dipping the earthworms for growth obtained by washing the skin after the step of removing the casting soil with the irradiation by a heater in an alkaline solution, thereby carrying out the removal of the residual casting soil and the body cavity fluids from the earthworms for growth.

Incidentally, by using the earthworms which have been subjected to a treatment for removing casting soil/body cavity fluids using an alkaline solution as a raw material for dry earthworm powder, it is possible to obtain dry earthworm powder having high enzymatic activity (that is, a high pharmacological action), as compared with a case of using earthworms which have not been subjected to the same treatment as a raw material.

The solute of the alkaline solution used in the present step is not particularly limited, and may be any one of sodium hypochlorite, sodium hydroxide, potassium hydroxide, calcium hydroxide, disodium hydrogen phosphate, sodium acetate, sodium citrate, sodium carbonate, sodium hydrogen carbonate, calcium chloride, and the like, and sodium hypochlorite is particularly preferred. Since sodium hypochlorite has been approved as a food additive and has high safety, and a solution thereof has a potent effect of removing body cavity fluids and a strong sterilization action.

FIG. 3 shows a change in the enzymatic activities of earthworms for growth, which have been subjected to a treatment for removing casting soil/body cavity fluids by the present step. Specifically, the earthworms for growth, which had been bred in a growth exclusive bed, were first subjected to removal of casting soil with the irradiation by a heater in the similar manner to the step of (1), and in the step of removing the residual casting soil/body cavity fluids of (2-1), sodium hypochlorite (NaClO) and sodium chloride (NaCl) were used as a solute of the alkaline solution, and the earthworms for growth were dipped in a sodium hypochlorite solution adjusted to 0.05%, 0.1%, 0.25%, or 0.5%, or a sodium chloride solution adjusted to 10% for 10 minutes, and subjected to removal of the residual casting soil/body cavity fluids. In addition, the earthworms for growth were washed with pure water, the earthworms for growth dipped in each of the solutions were then crushed by a homogenizer, the crushed products thereof were suspended in pure water, and the activity of the supernatant extracted by a centrifuge from the suspension was measured. Further, the amount of protein was also measured in order to determine a specific activity. In addition, as a control for comparison, the activity of the supernatant extracted from earthworms which had not been subjected to a treatment for dipping in a solution was also measured.

The measurement of the enzymatic activity and the measurement of the amount of protein were carried out in the same manner as the measurement in FIG. 2.

As shown in FIG. 3, the earthworms which had been dipped in each of the solutions could have an increase in total activity of the plasmin activity and the t-PA activity, and an increase in the specific activity, as compared with the earthworms which had not been subjected to a treatment for dipping in a solution. In addition, the sodium hypochlorite solution could increase the enzymatic activity even at a very low concentration, as compared with a sodium chloride solution and the sodium hypochlorite solution at a concentration of 0.1% also had an effect of improving the enzymatic activity to the same degree to a 10% sodium chloride solution. Thus, by carrying out the step of removing the residual casting soil/body cavity fluids by dipping in an alkaline solution in the present invention, it is possible to carry out the removal of the residual casting soil/body cavity fluids as well as the increase in the enzymatic activity of the earthworms for growth.

<Step of Producing Dry Earthworm Powder>

In the present step, earthworms for growth, from which the casting soil/body cavity fluids were removed by a step of a treatment for removing casting soil of earthworms, are first crushed by a known means such as a homogenizer, and crushed products thereof are suspended in pure water. Thereafter, the suspension is enclosed in a container such as a film and subjected to a pressurization treatment by a suitable pressurization device, and the suspension is sterilized. In addition, the supernatant is extracted from the suspension after the pressurization treatment by a centrifuge, and the supernatant is subjected to a freeze-dry treatment to produce dry earthworm powder.

In the production of dry earthworm powder, the earthworms can be subjected to removal of casting soil/body cavity fluids as well as to a sterilization treatment to obtain dry earthworm powder which is further not harmful to human bodies. Thus, in the present step, the earthworms for growth are subjected to a sterilization treatment by the pressurization treatment.

As a sterilization treatment, a heating treatment has been known, and the heating treatment has a risk of lowering the enzymatic activity by heating. Thus, with the sterilization by the pressurization treatment, sterilization can be reliably performed while not requiring heating leading to reduction of the enzymatic activity, and further, the enzymatic activity can be increased through the pressurization treatment.

Furthermore, the self-digestion of earthworms by the increase in the enzymatic activity by the pressurization treatment is promoted, and thus, the skin of the earthworms is lysated by the self-digestion during the pressurization treatment. Thus, a step of removing the skin of earthworms by filtration or the like, which was originally required, by carrying out the pressurization treatment, can be omitted. In the related art, there has been a risk of generation of loss of active ingredients due to the removal of the skin or reduction of the yield of a supernatant, from which dry earthworm powder is obtained by drying, but these problems can be avoided by employing a pressurization treatment.

Incidentally, by this pressurization treatment, there is an advantage that the odor of earthworms generated by crushing the earthworms to the processing into dry powder of earthworms can be reduced.

In the pressurization treatment of the present step, the pressure condition is preferably from 10 MPa to 500 MPa, and more preferably from 100 MPa to 200 MPa, and further, the pressurization times is preferably from 0.5 hours to 48 hours, and more preferably 1 hour to 2 hours.

Furthermore, the temperature condition is not particularly limited, but is preferably 0° C. to 70° C., and more preferably from 40° C. to 50° C., and by carrying out a pressurization treatment under this temperature condition, sterilization can be carried out more effectively. Further, at this temperature, there is no case where the enzymatic activity is reduced.

Moreover, in the present step, instead of a suspension of the crushed products of the earthworms for growth, the living organisms of the earthworms for growth may be enclosed in a film together with pure water to carry out a pressurization treatment. In this case, the same effect as a case where a suspension of the crushed products of the earthworms for growth is subjected to a pressurization treatment can be obtained. In addition, after the pressurization treatment, earthworms for growth having the skin lysated are crushed to obtain a suspension of crushed products, using pure water enclosed in the film together with the earthworms for growth, for example.

FIGS. 4 and 5 show a change in the numbers of bacteria and a change in the enzymatic activities, respectively, of earthworms for growth in the case of carrying out a pressurization treatment in the present step. The earthworms to be measured were earthworms for growth, from which casting soil/body cavity fluids had been removed. The earthworms were washed with pure water after the removal of casting soil/body cavity fluids and then crushed using a homogenizer, and the crushed products were suspended in pure water. Further, 35 ml of the suspension was then enclosed in a container of a plastic film and treated at 100 MPa and 50° C. for 1 hour to 2 hours. The activity and the number of bacteria of the supernatant extracted from the suspension by a centrifuge after the pressurization treatment were measured. In addition, as a control for comparison, the activity and the number of bacteria of the supernatant extracted from earthworms which had not been subjected to a pressurization treatment was also measured.

Examination of the number of bacteria was carried out by plating 1 mL of an earthworm crushing solution, which had been diluted with sterile water, onto a 3M Petrifilms AC Plate (manufactured by Sumitomo 3M Ltd.), culturing the plate in an incubator set at 30° C. for 48 hours, and then measuring the number of the colonies, in the case of examination of the number of general bacteria. Examination of the number of *Escherichia coli* was carried out by plating 1 mL of an earthworm crushing solution with had been diluted with sterile water onto a 3M Petrifilms RCC Plate (manufactured by Sumitomo 3M Ltd.), culturing the plate in an incubator set at 35° C. for 24 hours, and then measuring the number of the colonies.

The measurement of the enzymatic activity and the measurement of the amount of protein were carried out in the same manner as the measurement in FIG. 2.

As shown in FIG. 4, in the case where the pressurization treatment was not carried out, a number of general bacteria and *Escherichia coli* were detected, but in the case where the pressurization treatment was carried out for 1 hour, the number of general bacteria was significantly decreased and the number of *Escherichia coli* became negative. Further, in the case of carrying out the pressurization treatment for 2 hours, both of the number of general bacteria and the number of *Escherichia coli* became negative. Thus, the sterilization can be effectively carried out by carrying out the pressurization treatment.

As shown in FIG. 5, the protein concentration is reduced since the protein is precipitated by carrying out a pressurization treatment, but the total activity of the plasmin activity and the t-PA activity is increased and the specific activity is also increased. Thus, by carrying out a pressurization treatment, not only sterilization but also an increased enzymatic activity can be attained.

Other Embodiments

In the embodiments described above, *Eisenia fetida* was used as the earthworms in the production of dry earthworm powder, but the present invention is not limited thereto and for example, using a variety of earthworms used in health food/drugs, such as *Lumbricus rubellus*, may also be employed.

For the earthworm culturing process in the embodiment as described above, in the production of a growth exclusive bed used for breeding earthworms for growth, the pH value of a crushed product of a plant fiber material as a bed material was adjusted to around neutral values, but the present invention is not limited thereto. The pH value of the crushed product may be adjusted to various values according to the purpose.

For the earthworm culturing process in the embodiment as described above, in the production of a growth exclusive bed used for breeding earthworms for growth, it was described that a crushed product of a plant fiber material as a bed material was subjected to incorporation of a mineral fraction and adjustment of pH, but the present invention is not limited thereto. The crushed product of a plant fiber material may not be subjected to incorporation of a mineral fraction and adjustment of pH. Further, the bed material may not be crushed and may not be washed with sterile water.

In the step of removing casting soil with the irradiation by a heater in the embodiment as described above, it was described that the earthworms for growth were subjected to irradiation by a heater from the upper part of the growth exclusive bed while not taking out the earthworms for growth from the growth exclusive bed, but the present invention is not limited thereto. The earthworms for growth may be taken out from the growth exclusive bed and the earthworms for growth may be subjected to irradiation by a heater.

In the step of removing the residual casting soil/body cavity fluids by exposure to a vaporized volatile organic solvent in the embodiment as described above, it is described that cotton wool containing a volatile organic solvent was put into a bottle as a vaporization means, and the volatile organic solvent was vaporized in the bottle, but the present invention is not limited thereto and other vaporization means may be used.

In the step of removing the residual casting soil/body cavity fluids in the embodiment as described above, it was described that earthworms for growth were dipped in an alkaline solution, but the residual casting soil/body cavity fluids may be removed by exposing the earthworms for growth to a vaporized alkaline solution.

In the practice of the present invention, as the temperature conditions, the time conditions, the pressure conditions, and other conditions for a pressurization treatment for earthworms for growth, various conditions may be used.

For the earthworm culturing process in the embodiment as described above, the earthworms for growth which had been bred in a growth exclusive bed were subjected to removal of casting soil with the irradiation by a heater, exposure to a vaporized volatile organic solvent, or removal of the residual casting soil/body cavity fluids by dipping in an alkaline solution, and a sterilization treatment by a pressurization treatment to produce dry earthworm powder, but the present invention is not limited thereto. Dry earthworm powder may be produced by culturing the earthworms or subjecting the earthworms to a treatment for removing casting soil/body cavity fluids by a method different from the above-mentioned embodiment, and subjecting the earthworms to a sterilization treatment by the pressurization treatment.

INDUSTRIAL APPLICABILITY

The method for producing dry earthworm powder of the present invention may be used for the production of dry earthworm powder used in various applications in various fields.

The invention claimed is:

1. A method for producing dry earthworm powder comprising:
    subjecting live earthworms to a treatment that causes casting soil to be removed from the bodies of the earthworms;
    placing the treated earthworms in water, and subjecting the treated earthworms and water to pressurization under a pressure of 100 MPa to 500 MPa and a temperature of 40° C. to 70° C. for a time period of 0.5 to 48 hours to sterilize the earthworms;
    crushing the earthworms before or after said pressurization; and
    drying the crushed earthworms to produce the dry earthworm powder.

2. The method for producing dry earthworm powder according to claim 1, wherein the casting soil is removed from bodies of the earthworms by subjecting the earthworms to irradiation of heat rays by a heater.

3. The method for producing dry earthworm powder according to claim 2,
    wherein the casting soil is removed from the bodies of the earthworms by alternatingly subjecting the earthworms to the irradiation of heat rays by a heater and removing bed materials on a surface layer of a growth bed for growing earthworms.

4. The method for producing dry earthworm powder according to claim 1,
    further comprising removing residual casting soil and body cavity fluids of the earthworms from the bodies of the earthworms by exposing the earthworms to a vaporized volatile organic solvent before the earthworms are subjected to said pressurization.

5. The method for producing dry earthworm powder according to claim 1,
    further comprising removing residual casting soil and body cavity fluids of the earthworms from the bodies of the earthworms by dipping the earthworms in an alkaline solution before the earthworms are subjected to said pressurization.

6. The method for producing dry earthworm powder according to claim 1,
    wherein said pressurization is under a pressure of 100 MPa to 200 MPa.

7. The method for producing dry earthworm powder according to claim 4,
    wherein said pressurization is under a pressure of 100 MPa to 200 MPa.

8. The method for producing dry earthworm powder according to claim 5,
    wherein said pressurization is under a pressure of 100 MPa to 200 MPa.

9. The method for producing dry earthworm powder according to claim 1, wherein said time period is from 1 to 2 hours.

* * * * *